US00PP35645P2

(12) United States Plant Patent
Zwetsloot

(10) Patent No.: US PP35,645 P2
(45) Date of Patent: Feb. 6, 2024

(54) ***AGAPANTHUS* PLANT NAMED 'ZW12'**

(50) Latin Name: ***Agapanthus africanus* x *Agapanthus inapertus***
Varietal Denomination: ZW12

(71) Applicant: Jan Zwetsloot, Alphen aan den Rijn (NL)

(72) Inventor: Jan Zwetsloot, Alphen aan den Rijn (NL)

(73) Assignee: MARCO VAN NOORT BREEDING B.V., Warmond (NL)

( * ) Notice: Subject to any disclaimer, the term of this patent is extended or adjusted under 35 U.S.C. 154(b) by 0 days.

(21) Appl. No.: 18/114,898

(22) Filed: Feb. 27, 2023

(30) Foreign Application Priority Data

Aug. 20, 2022 (QZ) ..... PBR 20221960

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
See application file for complete search history.

*Primary Examiner* — Susan McCormick Ewoldt
(74) *Attorney, Agent, or Firm* — Penny J. Aguirre

(57) ABSTRACT

A new cultivar of *Agapanthus* plant named 'ZW12' that is characterized by its free flowering habit and continuously forms new inflorescences throughout the summer, its very compact plant habit, and its flowers with that are clear violet-blue in color with a lighter throat and tepal margins and central longitudinal stripe that is darker violet-blue in color.

2 Drawing Sheets

Botanical classification: *Agapanthus africanus* x *Agapanthus inapertus.*
Varietal denomination: 'ZW12'.

CROSS REFERENCE TO A RELATED APPLICATION

This application claims priority to European Community Plant Variety Office (CPVO) Plant Breeder's Rights Application No. 2022/1960, filed Aug. 20, 2022. The Applicant received the information for the Plant breeders' rights application directly from the Inventor.

BACKGROUND OF THE INVENTION

The present invention relates to a new and distinct cultivar of *Agapanthus* of hybrid origin, botanically known as *Agapanthus* 'ZW12', and will be referred to hereafter by its cultivar name, 'ZW12'. 'ZW12' represents a new perennial grown for landscape and container use.

The new cultivar was derived from a controlled breeding program by the Inventor in Voorhout, The Netherlands. The goal of the breeding program is to develop a new cultivar of *Agapanthus* with a very compact plant habit and floriferous blooming habit. The Inventor made a cross in July of 2006 between an unnamed and unpatented proprietary plant of *Agapanthus africanus* from the Inventor's breeding program as the female parent and unnamed and unpatented proprietary plant of *Agapanthus inapertus* from the Inventor's breeding program as the male parent. The Inventor selected 'ZW12' in July of 2008 as a single unique plant amongst the seedlings that resulted from the above cross.

Asexual propagation of the new cultivar was first accomplished by division by the Inventor in Voorhout, The Netherlands in May of 2020. Asexual propagation by division and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'ZW12' as a distinct cultivar of *Agapanthus.*

1. 'ZW12' exhibits a free flowering habit and continuously forms new inflorescences throughout the summer.
2. 'ZW12' exhibits a very compact plant habit.
3. 'ZW12' exhibits flowers with that are clear violet-blue in color with a lighter throat and tepal margins and central longitudinal stripe that is darker violet-blue in color.

The female parent of 'ZW12' differs from 'ZW12' in having a much less compact plant habit, peduncles that are thinner, and individual flowers that are smaller in size. The male parent of 'ZW12' differs from 'ZW12' in having inflorescences that are larger in size and flowers that are solid blue in color. 'ZW12' can be most closely compared to the *Agapanthus* cultivars 'Appy' (not patented) and 'Sandy' (not patented). 'Appy' and 'Sandy' are both similar to 'ZW12' in having free flowering habits. 'Appy' differs from 'ZW12' in having a taller plant height and a less remontant blooming habit. 'Sandy' differs from 'ZW12' in having a taller plant height, a later flowering season, a less remontant in blooming habit, and flowers that are lighter and grey-blue in color.

BRIEF DESCRIPTION OF THE DRAWINGS

The accompanying color photographs illustrate the overall appearance and distinct characteristics of the new

*Agapanthus*. The photographs were taken of a plant 2 years in age of 'ZW12' as grown outdoors in a 23-cm container in Warmond, The Netherlands.

Figure 1:
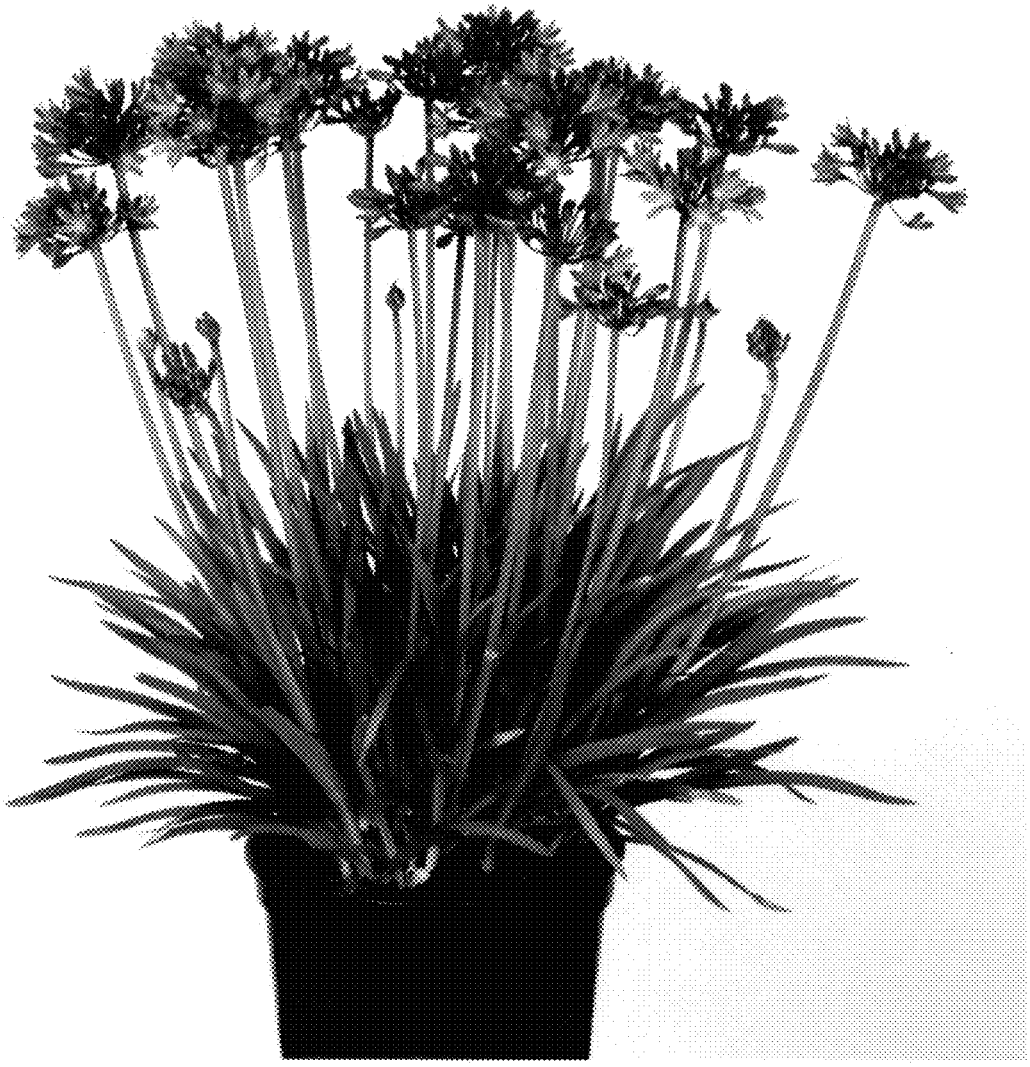

The photograph in FIG. 1 provides a side view of a plant of 'ZW12' in bloom.

Figure 2:
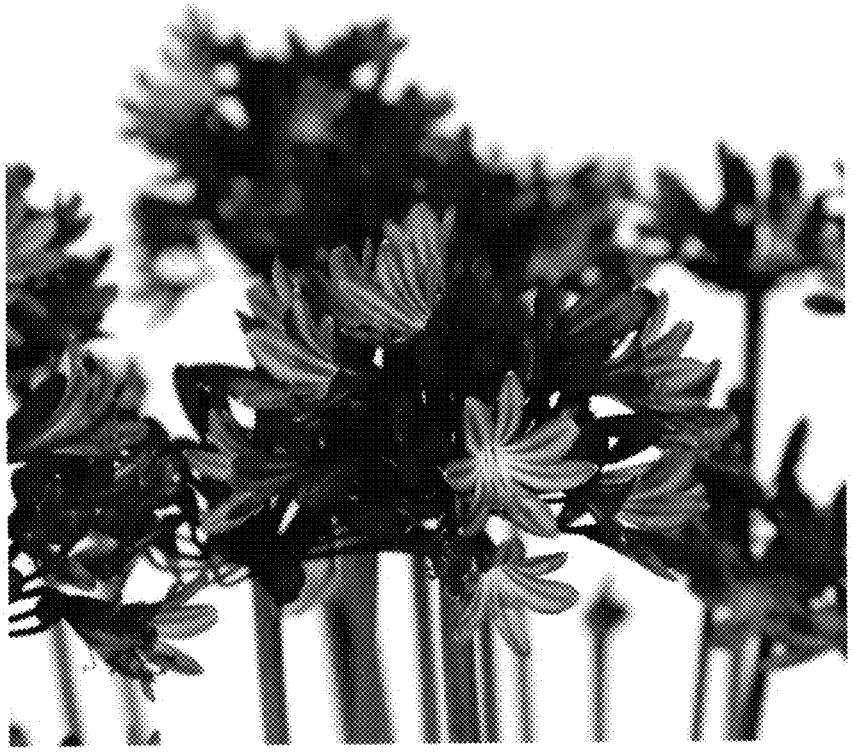

The photograph in FIG. 2 provides a close-up view of the inflorescences of 'ZW12'.

Figure 3:
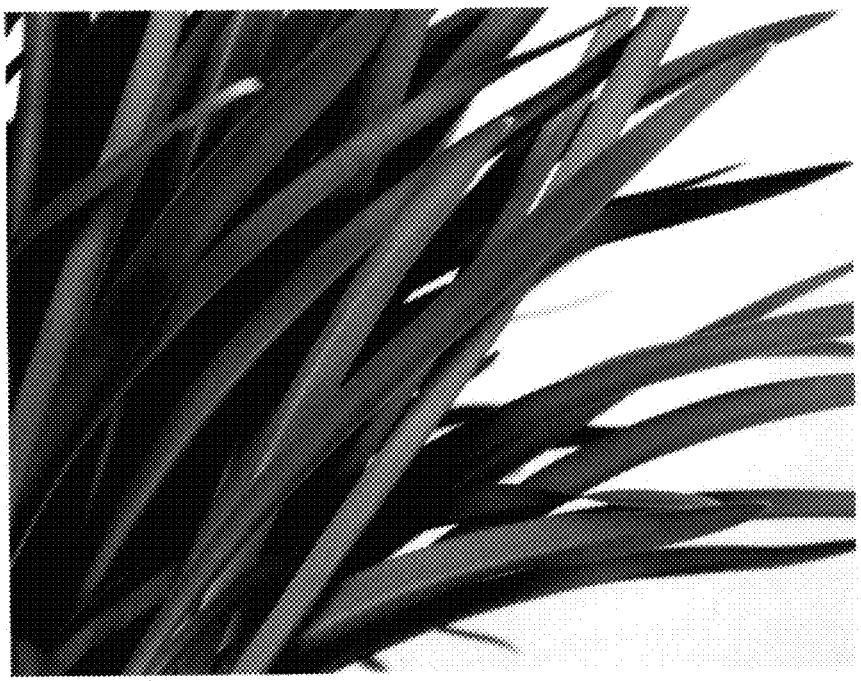

The photograph in FIG. 3 provides a close-up view of the foliage of 'ZW12'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 2-year-old plants of 'ZW12' as grown outdoors in 23-cm containers in Warmond, The Netherlands. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Blooming period*.—Early summer into fall in The Netherlands.

*Plant type*.—Semi-deciduous (climate dependent) herbaceous perennial.

*Plant habit*.—Basal rosettes with inflorescences emerging from the rosette center.

*Height and spread*.—An average of 60 cm in height and width.

*Cold hardiness*.—At least to U.S.D.A. Zone 8.

*Diseases and pests*.—No susceptibility and resistance to diseases or pests has been observed.

*Root description*.—Thick and fleshy, 161C in color.

*Propagation*.—Tissue culture and division.

*Growth rate*.—Vigorous.

*Number of shoots* (*rosettes*).—An average of 35.

*Root development*.—4 to 5 weeks for root initiation, 10 to 12 weeks to produce a rooted cutting.

Foliage description:

*Leaf shape*.—Ligulate.

*Leaf division*.—Simple.

*Leaf base*.—Truncate.

*Leaf arrangement*.—In basal rosettes, equitant.

*Leaf apex*.—Acute.

*Leaf aspect*.—Moderately carinate, slightly curved.

*Leaf venation*.—Parallel, upper surface; 137A, lower surface; 144B.

*Leaf margins*.—Entire, unlobed.

*Leaf size*.—Up to 29 cm in length and up to 1.4 cm in width.

*Leaf surface*.—Smooth, glabrous, and dull on upper and lower surface.

*Leaf number*.—Average of 6 per rosette.

*Leaf color*.—Young leaves upper surface; 143A, young leaves lower surface; 138A, mature leaves upper surface; 137B, mature leaves lower surface; a blend of 137B and 146A.

*Leaf attachment*.—Sessile to base.

Flower description:

*Inflorescence type*.—Umbel, flattened hemispherical to hemispherical.

*Flower fragrance*.—None.

*Flower type*.—Rotate, campanulate, base of tepals fused 36.5%.

*Flower number*.—An average of 75 flowers per umbel, 2,300 per plant.

*Inflorescence size*.—Average of 7 cm in height, 10.3 cm in diameter.

*Flower size*.—An average of 2.7 cm in depth, 3.3 cm in diameter, tube 1.1 cm in length and 4.5 mm in diameter, throat 4 mm in diameter.

*Lastingness of inflorescence*.—Average 14 days, an average of 10 days as a cut flower, self-cleaning.

*Flower aspect*.—Slightly outward to upright.

*Peduncle*.—1 per rosette, strong, oval in shape, strong, average angle of 80°, surface is smooth, glabrous, matte, slightly glaucous covered with a very thin matte waxy layer 194B, average of 48.2 cm in length and 7 mm in width at distal region and 9 mm in width at proximal region, color; 144A, finely dotted and tinged with a blend of 200A and 203A.

*Pedicels*.—Strong, average of 2.3 cm in length and 2 mm in width, held erect to outward (0° to 120°), moderately glossy, smooth and glabrous, color; upper surface 203B, lower surface 143C.

*Flower buds*.—Oblanceolate in shape, surface is smooth, slightly velvety, moderately glossy, average of 1.9 cm in length and 6 mm in width, color; N89C, darker towards the top N89B, base N89A.

*Tepals* (*perianth*).—6 lobes in 2 whirls, rotate, oblanceolate in shape with lower tepals slightly falcate, lower 36.5% fused, entire margins, apex is acute to bluntly acute, glabrous, slightly velvety, slightly glossy, and non-rugose on inner and outer surfaces, an average of 3 cm in length and 6 mm in width, color: color upper surface when opening upper and lower surface upper and lower tepals; N89D and N89C towards apex, color when opening lower surface; lower tepals N89C and N89B towards apex with longitudinal central stripe N89A, upper tepals N89C with longitudinal central stripe N89A, color fully open upper surface; lower tepals 93C fading toward throat to 91B with margins and longitudinal central stripe N89B, upper tepals 94C and fading towards throat to 91C with margins N89C and longitudinal central stripe N89B, color fully lower surface; lower tepals N89C with longitudinal central stripe N89A, upper tepals N89D with longitudinal central stripe N89B, color when fading upper and lower tepals both surfaces; 86A to 86B, throat color 91C with longitudinal central stripe N89B, tube color; outer surface N89B to 89D and inner surface 91C to 91D.

*Bracts*.—Broad ovate in shape, acuminate apex, truncate base, glabrous and matte surface, 3 cm in length, 2 cm in width, color; N155A, veins 138A, veins 79C.

Reproductive organs:

*Gynoecium*.—Pistil; 1, average of 1.2 cm in length, stigma; club-shaped, 91C in color, style; 1.1 cm in length, color; 91A, base 91D, ovary; oblong in shape, 1 cm in length, 4 mm in width and 150B in color.

*Androecium*.—Stamens; 6, anthers; dorsifixed, oblong in shape, average of 1.5 mm in length, 0.8 mm in width, 203A in color, filament; 1.4 cm in length, color; 92A, base NN155D, pollen; moderate in quantity and 151D in color.

*Fruit/seed*.—None observed to date.

It is claimed:

1. A new and distinct cultivar of *Agapanthus* plant named 'ZW12' as herein illustrated and described.

* * * * *